(12) United States Patent
Urbanski et al.

(10) Patent No.: US 10,779,883 B2
(45) Date of Patent: Sep. 22, 2020

(54) EPICARDIAL ACCESS SYSTEM AND METHODS

(71) Applicant: Baylis Medical Company Inc., Montreal (CA)

(72) Inventors: John Paul Urbanski, Toronto (CA); Brock Miller, Toronto (CA); Rund Abou-Marie, Toronto (CA)

(73) Assignee: Baylis Medical Company Inc., Mississauga (CA)

( * ) Notice: Subject to any disclaimer, the term of this patent is extended or adjusted under 35 U.S.C. 154(b) by 270 days.

(21) Appl. No.: 15/754,030

(22) PCT Filed: Sep. 9, 2016

(86) PCT No.: PCT/IB2016/055404
§ 371 (c)(1),
(2) Date: Feb. 21, 2018

(87) PCT Pub. No.: WO2017/042743
PCT Pub. Date: Mar. 16, 2017

(65) Prior Publication Data
US 2018/0206910 A1 Jul. 26, 2018

Related U.S. Application Data

(60) Provisional application No. 62/216,059, filed on Sep. 9, 2015.

(51) Int. Cl.
*A61B 18/14* (2006.01)
*A61B 18/00* (2006.01)
(Continued)

(52) U.S. Cl.
CPC ...... *A61B 18/1477* (2013.01); *A61B 18/1492* (2013.01); *A61B 17/3417* (2013.01);
(Continued)

(58) Field of Classification Search
CPC ............ A61B 18/1477; A61B 18/1492; A61B 17/3417; A61B 2018/00083;
(Continued)

(56) References Cited

U.S. PATENT DOCUMENTS 4,774,949 A 10/1988 Fogarty
5,007,908 A * 4/1991 Rydell ............... A61B 18/1477
606/47
(Continued)

OTHER PUBLICATIONS

Patent Cooperation Treaty, International Preliminary Report on Patentability, International Application No. PCT/IB2016/055404, dated Dec. 8, 2016.
(Continued)

*Primary Examiner* — Michael F Peffley
(74) *Attorney, Agent, or Firm* — Glenn Arnold; Vincent Man; Samuel Tekie (57) ABSTRACT

A method and apparatus are disclosed for a needle for gaining access to the pericardial cavity of a heart. The needle includes an elongate member (e.g. a main shaft) defining a lumen and a side-port in communication with the lumen; a blunt atraumatic tip for delivering energy for puncturing tissue; and a guiding surface (e.g. a ramp) for directing a device (e.g. a guidewire) through the side-port. The method includes using the needle for tenting a pericardium and delivering energy for puncturing the pericardium, and advancing a guidewire or other device through the needle and into the pericardial cavity.

16 Claims, 9 Drawing Sheets

Detail A-V1

Detail A-V2

(51) Int. Cl.
  *A61B 17/34* (2006.01)
  *A61B 90/00* (2016.01)
  *A61B 17/3207* (2006.01)

(52) U.S. Cl.
  CPC ............ *A61B 2017/320791* (2013.01); *A61B 2018/00083* (2013.01); *A61B 2018/00196* (2013.01); *A61B 2018/00351* (2013.01); *A61B 2018/00363* (2013.01); *A61B 2018/00577* (2013.01); *A61B 2018/00601* (2013.01); *A61B 2090/3966* (2016.02)

(58) Field of Classification Search
  CPC ........... A61B 2018/00196; A61B 2018/00351; A61B 2018/00363; A61B 2018/00577; A61B 2018/00601; A61B 2017/320791; A61B 2090/3966
  USPC ...................................... 606/32–50
  See application file for complete search history.

(56) References Cited

U.S. PATENT DOCUMENTS

| | | | |
|---|---|---|---|
| 5,163,921 A | 11/1992 | Feiring | |
| 5,558,673 A * | 9/1996 | Edwards | A61B 18/1477 606/41 |
| 5,827,216 A | 10/1998 | Igo et al. | |
| 5,972,013 A * | 10/1999 | Schmidt | A61B 17/3417 604/164.01 |
| 6,146,380 A * | 11/2000 | Racz | A61N 1/0551 606/41 |
| 6,162,195 A | 12/2000 | Igo et al. | |
| 6,423,051 B1 | 7/2002 | Kaplan et al. | |
| 6,666,844 B1 | 12/2003 | Igo et al. | |
| 6,770,070 B1 * | 8/2004 | Balbierz | A61B 10/04 600/566 |
| 7,166,104 B2 * | 1/2007 | Young | A61B 18/1477 606/41 |
| 7,191,015 B2 | 3/2007 | Lamson et al. | |
| 7,229,438 B2 * | 6/2007 | Young | A61B 18/148 606/41 |
| 7,736,347 B2 | 6/2010 | Kaplan et al. | |
| 7,797,059 B1 | 9/2010 | Bornzin et al. | |
| 7,846,088 B2 | 12/2010 | Ness | |
| 8,211,084 B2 | 7/2012 | Kassab et al. | |
| 8,241,276 B2 * | 8/2012 | Epstein | A61B 18/1477 606/41 |
| 8,282,565 B2 | 10/2012 | Mahapatra et al. | |
| 8,311,648 B1 | 11/2012 | Chitre et al. | |
| 8,317,810 B2 | 11/2012 | Stangenes et al. | |
| 8,475,468 B2 | 7/2013 | Leckrone et al. | |
| 8,538,555 B1 | 9/2013 | Chitre et al. | |
| 8,603,031 B2 | 12/2013 | Callas et al. | |
| 8,874,237 B2 | 10/2014 | Schilling | |
| 8,906,056 B2 | 12/2014 | Gillies et al. | |
| 8,979,842 B2 | 3/2015 | McNall, III et al. | |
| 2003/0187461 A1 | 10/2003 | Chin | |
| 2005/0261673 A1 * | 11/2005 | Bonner | A61B 18/1485 606/41 |
| 2007/0293924 A1 | 12/2007 | Belden et al. | |
| 2009/0198252 A1 | 8/2009 | Selfert et al. | |
| 2010/0331854 A1 | 12/2010 | Greenberg et al. | |
| 2012/0130366 A1 | 5/2012 | Carroll et al. | |
| 2016/0242661 A1 * | 8/2016 | Fischell | A61B 5/04001 |

OTHER PUBLICATIONS

European Patent Office, Communication pursuant to Rule 161(2) and 162 EPC for counterpart European Application No. 16843791, dated Apr. 25, 2018.

* cited by examiner

EPICARDIAL ACCESS SYSTEM AND METHODS

TECHNICAL FIELD

This disclosure relates to the field of surgical needles. More specifically, this disclosure relates to surgical needles that use energy for puncturing.

BRIEF DESCRIPTION OF THE DRAWINGS

In order that the invention may be readily understood, embodiments of the invention are illustrated by way of examples in the accompanying drawings, in which:

FIG. 1, consisting of FIGS. 1A-1D, as well as detail views A-V1, A-V2, C1 and C2, is an illustration of a needle having a side-port in accordance with an embodiment of the invention;

FIG. 3, consisting of FIGS. 3A-3H, is an illustration showing the steps in a method of using a needle in accordance with an embodiment of the invention;

FIG. 4, consisting of FIGS. 4A-4F, is an illustration showing the use of ECG in accordance with an embodiment of the invention;

FIG. 6, consisting of FIGS. 6A-6E, is an illustration showing the steps in a method of using a needle in accordance with an alternative embodiment of the invention; and FIG. 7, consisting of FIGS. 7A-7D, shows ECG readings in accordance with an embodiment of the invention.

DETAILED DESCRIPTION

Minimally invasive access to the pericardial space is required for diagnosis and treatment of a variety of arrhythmias and other conditions. Access to the space may be initiated using a large diameter (for example, about 17Ga) Tuohy-style needle via the subxiphoid approach. A guidewire (for example, about 0.032 inches (about 0.81 mm) in outer diameter) is then advanced to the heart through the needle lumen. After gaining access to the pericardial space, the operator removes the Tuohy-needle then advances and secures a sheath (for example, 8.5Fr) to facilitate use of treatment devices such as ablation and mapping catheters.

Mechanical puncture using large bore needles, as described above, is associated with a high clinical complication rate. Although the stiff needle provides some stability and some tactile feedback to the user, unwanted tissue damage is possible if the needle inadvertently punctures or unintentionally lacerates tissue.

As a consequence of the challenges and uncertainties of using mechanical puncture for accessing the pericardial space, physicians may resort to common endocardial ablation in situations where epicardial ablation is a preferred treatment, such as ventricular tachycardias. New devices or methods to improve the safety and predictability of gaining access to the pericardial space would be of benefit.

The problem of improving the ease of use, safety, and predictability of gaining access to the epicardium is solved, at least in part, by a needle for gaining epicardial access, the needle having an elongate member (e.g. a main shaft) defining a lumen and a side-port in communication with the lumen; a blunt atraumatic tip for delivering energy for puncturing tissue; and a guiding surface (e.g. a ramp) for directing a device (e.g. a guidewire) through the side-port.

The present inventors have conceived, and reduced to practice, embodiments of such a medical device. Some embodiments of the needle have a blunt tip of 17, 18 19, or 19.5 Ga. The blunt tip prevents any premature mechanical puncture to the pericardium when pressed against it. Also, a needle with a blunt tip provides better tactile feedback than a needle with a sharp tip. The side-port allows delivery of contrast agent and facilitates deployment of a device (e.g. a guidewire) through the needle to confirm access to the pericardial space. Physicians typically use fluoroscopy to check that the guidewire (or other device) is wrapped around the heart to confirm pericardial access. Physicians may also confirm access via tactile feedback which may indicate incorrect needle position or obstruction. Physicians may also deliver contrast medium to confirm access and determine needle location.

In one broad aspect, embodiments of the present invention comprise a needle for gaining access to the pericardial cavity of a heart, the needle having a blunt tip for delivering energy for puncturing, and a side-port for confirming, gaining, or facilitating epicardial access.

As a feature of this aspect, the needle comprises a guiding surface feature (e.g. a ramp) within the side-port configured to guide the guidewire (or other device) out the side of the needle and in a forward direction. Some embodiments of the guiding surface have a generally S-shaped surface.

In a second broad aspect, embodiments of the present invention comprise a needle for gaining epicardial access, the needle comprising: an elongate member defining a lumen and a side-port in communication with the lumen; a blunt tip for delivering energy for puncturing tissue; and a guiding surface for directing a device through the side-port. In some embodiments, the elongate member is comprised of a metal, and the needle further comprises an insulation covering outside of the elongate member, with the blunt tip being electrically exposed to define an electrode, wherein the needle is operable for delivering energy through a metal side wall of elongate member to the electrode. In some such embodiments, the electrode has greater radiopacity than the elongate member. Some embodiments of this broad aspect include an insulation portion covering a proximal part of the side-port to define an aperture, with the insulation portion being configured to reduce abrasive friction between the device and a proximal edge of the side-port as the device travels through the side-port.

As features of the second broad aspect, some embodiments further comprise insulation on an inner surface of the elongate member adjacent to the side-port to reduce electrical leakage, with some embodiments further comprising insulation on the inner surface of most or substantially all the elongate member to reduce electrical leakage, and some embodiments including a part of the elongate member adjacent and distal of the side-port being electrically exposed to define an elongate member exposed portion.

As features of the second broad aspect, some embodiments include the lumen terminating at the side-port. Some embodiments include a single side-port operable for the device to travel therethrough. In some embodiments, the side-port is capsule-shaped. Some examples have a distal edge of the side-port including a bevel, and in some such examples, the bevel includes a combination of rounded and flat portions.

Some embodiments of the needle comprise a distal edge of the side-port being located at a distance of about 0.050 to 0.125 inches (about 1.27 to 3.18 mm) from an electrode distal tip, and in some such embodiments, the distal edge of the side-port is located at a distance of about 0.090 inches (about 2.29 mm) from the electrode distal tip.

As features of the second broad aspect, some embodiments include a proximal edge of the side-port being beveled; the guiding surface having a generally S-shaped surface; and an insulation portion covering a proximal part of the side-port and a distal end of the guiding surface being beveled, whereby the device is guided out of a side of the needle and in a forward direction when advanced out of the side-port.

In accordance with an embodiment of the present invention, a method is disclosed for accessing a pericardial cavity, the method comprising the steps of: (1) contacting a pericardium with a needle, (2) tenting the pericardium with the needle and delivering energy through a blunt tip of the needle, (3) puncturing the pericardium with the needle and injecting a contrast flow into a pericardial cavity through a side-port of the needle, (4) advancing a guidewire through the needle and into the pericardial cavity, and (5) withdrawing the needle while leaving the guidewire in the pericardial cavity.

In accordance with an embodiment of the present invention, method is disclosed for accessing a pericardial cavity, the method comprising the steps of: (1) contacting a pericardium with a needle, (2) tenting the pericardium with the needle and delivering energy through a blunt tip of the needle, (3) puncturing the pericardium with the needle and injecting a contrast flow into a pericardial cavity through a side-port of the needle, (4) advancing a small diameter guidewire into the pericardial cavity, (5) withdrawing the needle and advancing a dilator to dilate the puncture through the pericardium, (6) advancing a sheath over the dilator into pericardial cavity, (7) withdrawing the small diameter guidewire and advancing a relatively larger guidewire into the pericardial cavity, and (8) withdrawing the sheath.

In a further broad aspect, embodiments of the present invention are for a method having the steps of contacting a pericardium with a needle, using the needle for tenting the pericardium and delivering energy, using the needle for puncturing the pericardium and injecting a contrast flow into a pericardial cavity, advancing a guidewire (or other device) through the needle and into the pericardial cavity, and withdrawing the needle while leaving the guidewire (or other device) in the pericardial cavity.

As features of this aspect, some embodiments of the method further include the steps of advancing a mapping catheter or some other diagnostic device, and/or advancing an ablation catheter or some other treatment device, and/or placing leads or other medical devices.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1A:
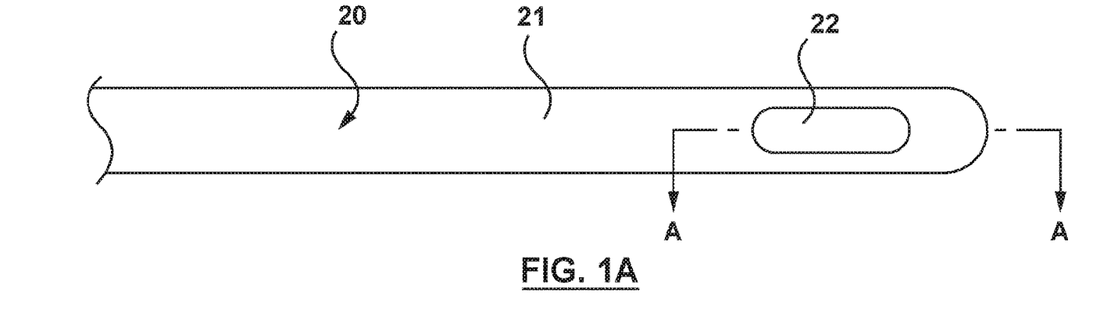
Figure 1B:
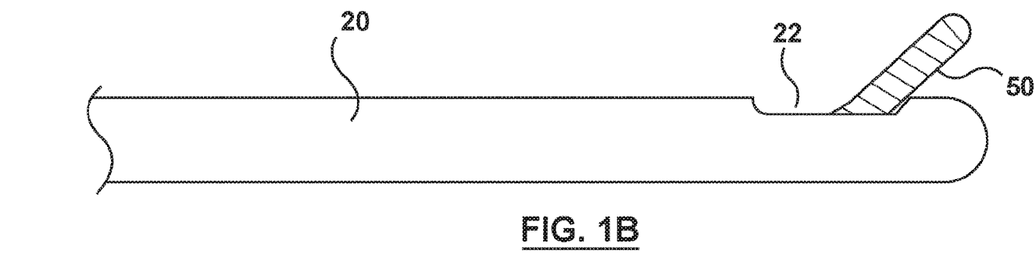

FIG. 1A shows a top view of a needle 20 having a side-port 22 in elongate member 21. FIG. 1B shows a side view of the same needle with a guidewire 50 extending out of side-port 22. The side-port of FIGS. 1A and 1B is a slotted hole. The dimensions of the slot are dependent on the needle gauge and guidewire outer diameter. Some embodiments of needle 20 are 17Ga, have a side-port width of about 0.036 inches (about 0.91 mm), a radius of about 0.018 inches (about 0.46 mm), a slot length of about 0.180 inches (about 4.57 mm), and can accommodate deployment and retraction of a 0.032 inches (about 0.81 mm) guidewire, and of guidewires having a smaller outer diameter. Such an embodiment may also accommodate, with a smaller clearance, a guidewire with an outer diameter of 0.035 inches (about 0.89 mm). Guidewires used in the disclosed method are typically comprised of spring stainless steel. In some embodiments, the distal tip of the guidewire is made of nitinol to provide a softer tip than steel. Some alternative embodiments comprise an insulated guidewire having a lubricous coating on the insulation. Embodiments of needle 20 typically have only a single side-port operable for advancing a guidewire (or other device) therethrough.

While this disclosure, for explanatory purposes, focuses on the use of needle 20 with guidewires, other devices can be advanced through needle, for example, flexible devices operable to delivery energy or monitor physiological variables.

The embodiment of the side-port 22 of FIG. 1A is a rounded slot or a slotted hole (i.e. capsule-shaped) having a constant side-port width. This configuration provides a flat wall with a minimal edge profile, thereby reducing the potential for generating debris when deploying or retracting a guidewire. Typically, side-port 22 and guidewire 50 are configured such that the clearance of the side-port 22 from the guidewire will be at least about 0.001 inches (about 0.025 mm). If using a smaller outer diameter guidewire, the clearance will be greater.

Detail A-V1 and detail A-V2 show alternative views for cut-away line A-A of FIG. 1A. Details A-V1 and A-V2 illustrate a guiding surface 24 (or ramp) within side-port 22, which functions to guide an advancing guidewire 50 through side-port 22. The guiding surface embodiment may be straight (e.g. detail A-V1) or curved (e.g. detail A-V2). The portion of guiding surface 24 visible from external side-view (from outside of the needle) has a length of about 0.020 inches (about 0.51 mm) for the embodiment of FIG. 1B. Please note, that while not all of the figures show a layer of insulation since it is not necessary for an understanding of the features illustrated by those figures, typical embodiments of needle 20 include insulation.

Guidewire 50 is placed under a bending moment when exiting the side port. To reduce this force, a bevel 26 (shown in FIG. 5) is located at the distal edge of side-port 22. In some embodiments, a bevel 26 of 10 degrees is located about 0.020 inches (about 0.51 mm) from the distal edge of side-port 22. Some such embodiments have been shown to be effective in reducing the bending moment. In some embodiments the bevel is generally flat, while in other embodiments the bevel is rounded, and in yet further embodiments the bevel includes a combination of rounded and flat portions.

Figure 5:
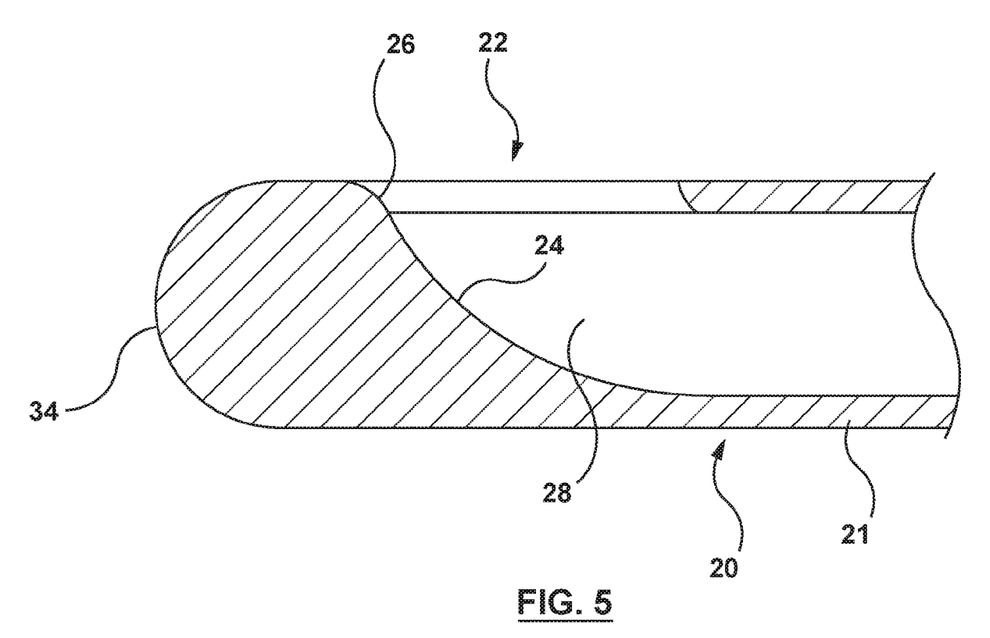
FIG. 5 is an illustration showing an enlarged view of a side-port in accordance with an embodiment of the invention.
Figure 6A:
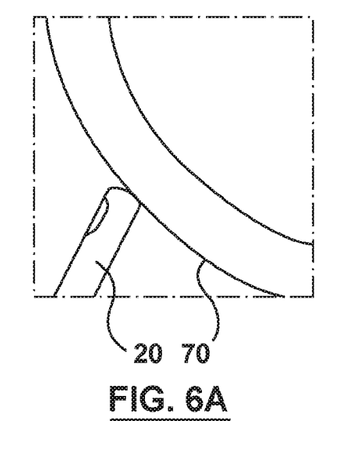
Figure 6B:
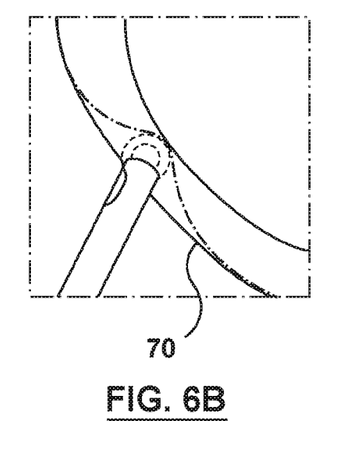
Figure 6C:
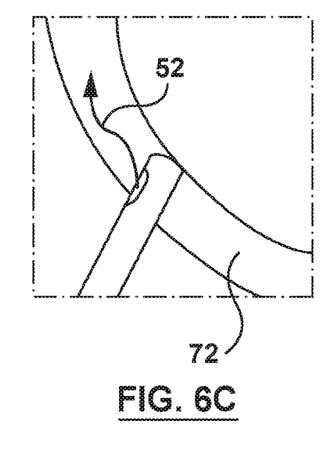
Figure 6D:
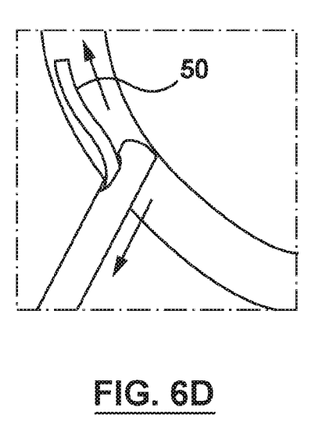
Figure 6E:
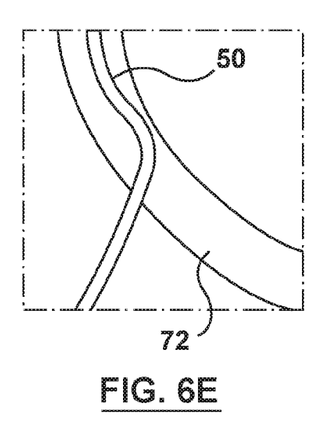
Figure 7A:
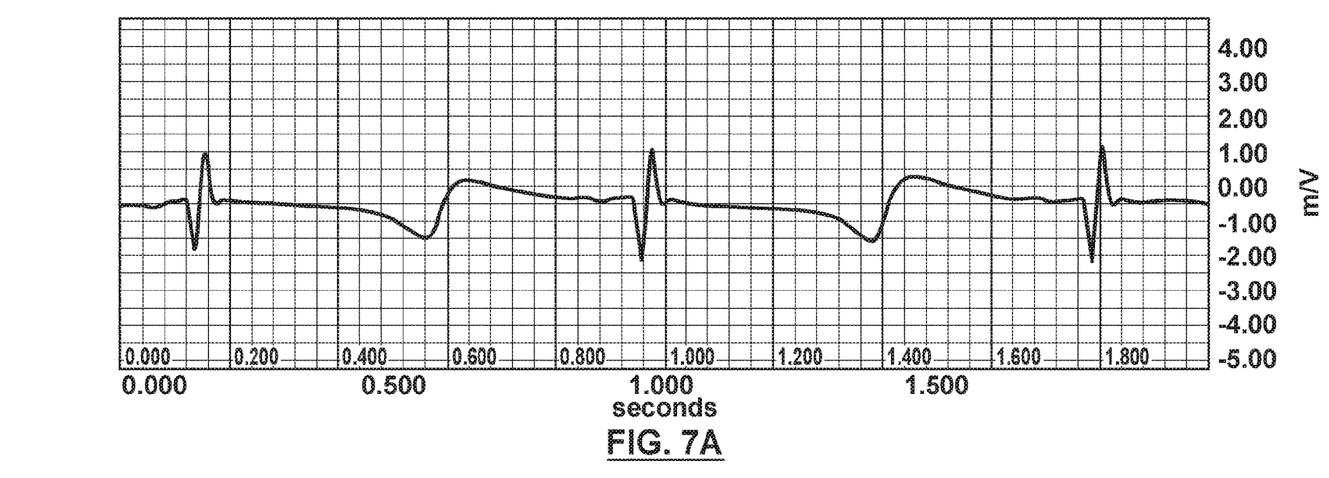
Figure 7B:
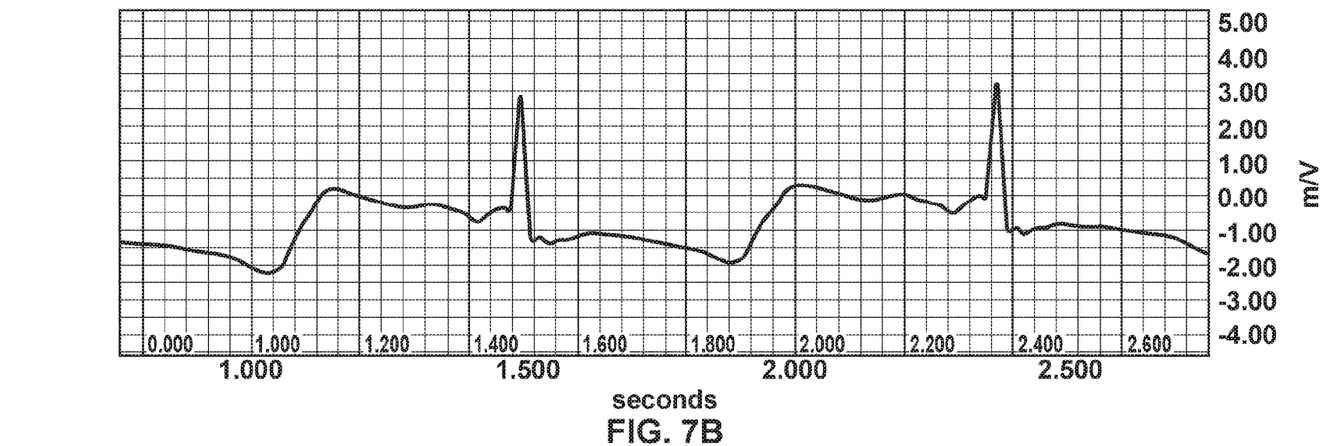
Figure 7C:
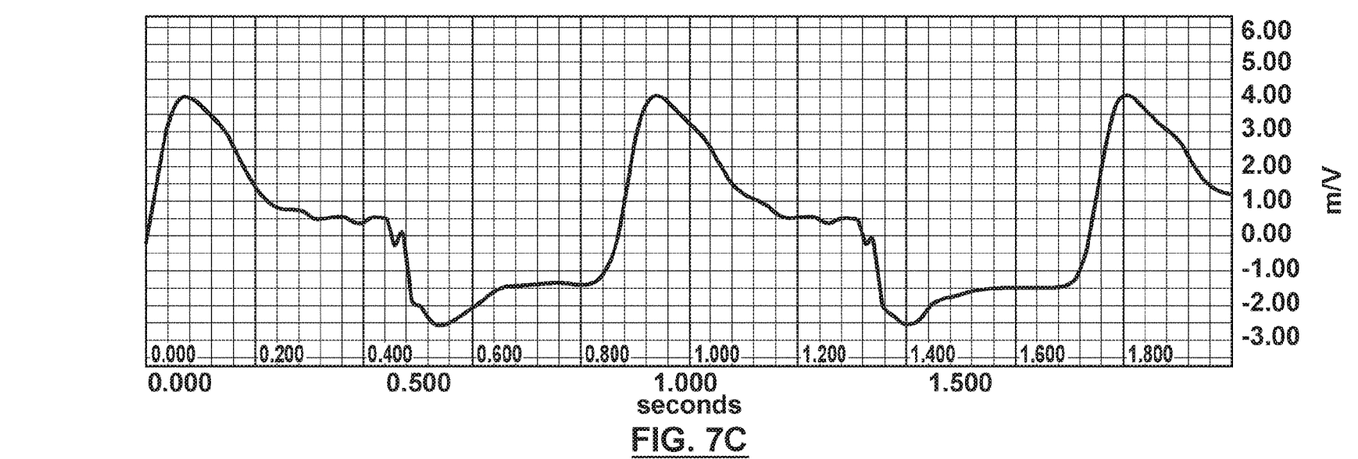
Figure 7D:
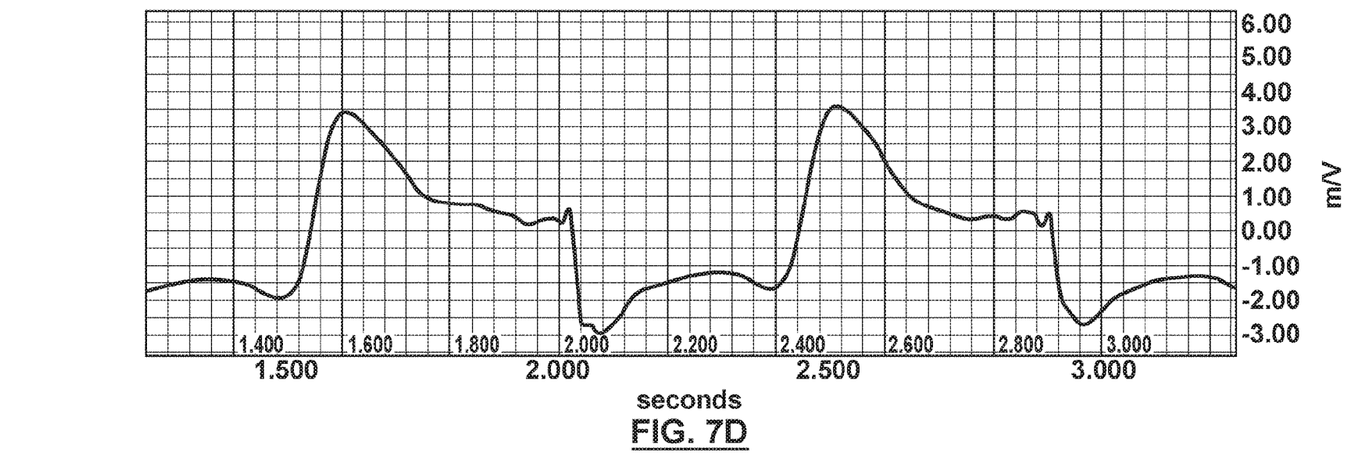

FIG. 5 is a cut-away view including distal tip 34 of needle 20, wherein elongate member 21 defines lumen 28, guiding surface 24, and side-port 22. The embodiment of guiding surface 24 of FIG. 5 has a generally S-shaped surface. In general, side-port 22 is located close to the distal tip of the needle, which is advantageous for confirming the position of distal tip 34 because it allows contrast fluid to be delivered close to the needle's tip. In contrast, a device having a side-port that is relatively further away from the tip is more likely to encounter a situation where the side-port is still covered by tissue even though the distal tip has punctured a layer of tissue. A side-port 22 located close to the distal tip, in combination with the previously described bevel 26, also allows for a curved or tip wire extended through side-port 22 to travel a short distance forward before curving, which prevents potential piercing of the epicardium with the wire tip. While a curved tip wire that easily bends or is floppy at the distal tip is advantageous for reducing unwanted tissue trauma, needle 20 may also be used with guidewire having a straight tip.

Figure 1C:
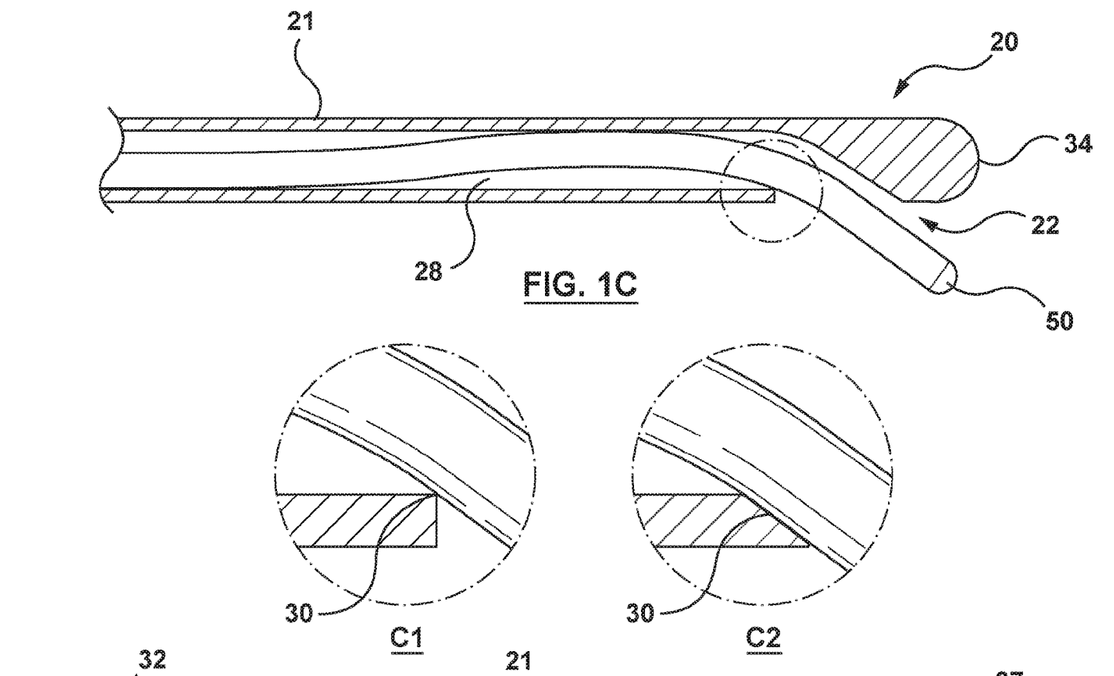

FIG. 1C is a cross-section showing a guidewire 50 that has been advanced through the lumen 28 and the side-port of needle 20. Enlarged sections C1 and C2 show guidewire 50 in contact with two different embodiments of the proximal edge 30 of side-port 22. Enlarged section C1 includes a proximal edge 30 having an approximately 90° angle. This angle is sharp enough to scrape a guide-wire as it is advanced or retracted through the side-port, which may result in some debris creation. It is advantageous for proximal edge 30 to be beveled (as shown, for example, in enlarged section C2) to reduce debris generation when translating the guidewire through the needle. Some embodiments include a straight beveled edge or a rounded bevel located about 0.020 inches (about 0.51 mm) from a proximal edge 30. In some such embodiments, these bevels have proven effective in reducing debris formation.

Figure 1D:
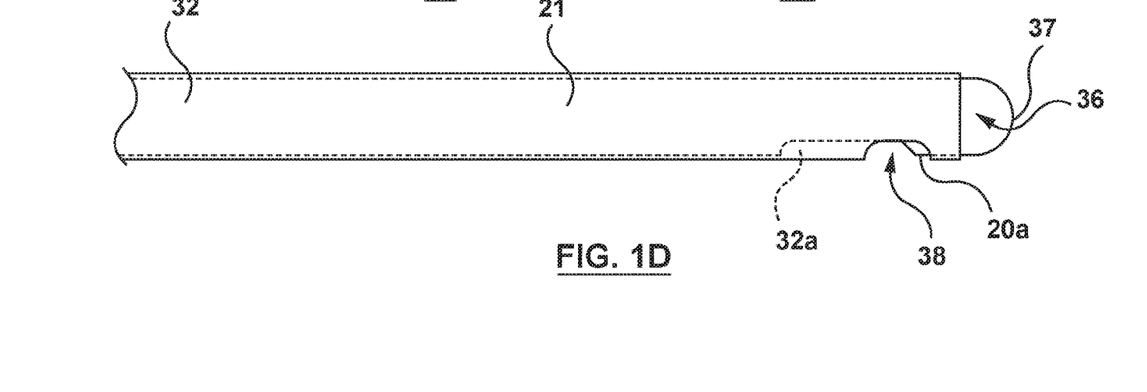

FIG. 1D illustrates needle 20 with insulation 32 (typically a polymer) covering the needle shaft, leaving an area around side-port 22 exposed, and a distal tip area exposed to define an electrode 36 which may be used for channeling into and puncturing tissue. In some alternative embodiments, insulation 32 is a ceramic.

Typical embodiments of needle 20 have a elongate member 21 (i.e. a main shaft) comprised of 304, 316 or 317 stainless steel, and an electrode 36 comprised of the same steel as the elongate member 21, with electrode 36 being dome welded. Alternative embodiments of elongate member 21 are comprised of other metals, including copper, titanium and nickel-titanium alloys, amongst others. In typical embodiments, energy (e.g. electricity) is delivered to electrode 36 through the metal side wall of needle 20. In some alternative embodiments, the needle's elongate member 21 is comprised of a stiff polymer and electrical energy is delivered to electrode 36 through an electrically conductive wire. Some alternative embodiments have an electrode 36 comprised, at least in part, of material more radiopaque than the elongate member such as platinum, platinum and Iridium alloys, gold, or silver to provide radiopaque visibility under fluoroscopy to determine the location of the needle's tip (i.e. the electrode has greater radiopacity than the elongate member). Such materials also improve reduction potential when collecting ECG data. Round tipped electrodes and the use of such round tipped electrodes for cutting tissue is described in U.S. Pat. No. 8,192,425, which is incorporated-by-reference herein in its entirety.

In one specific embodiment of needle 20, side-port 22 in elongate member 21 has a length of about 0.180 inches (about 4.57 mm), the distance between side-port 22 and electrode 36 is about 0.065 inches (about 1.65 mm), electrode 36 has a hemispherical shape with a radius of about 0.025 inches (about 0.64 mm), whereby distal tip 34 of needle 20 has an outer diameter of about 0.050 inches (about 1.25 mm), and there is distance of about 0.090 inches (about 2.29 mm) between electrode distal tip 37 (FIG. 1D) and side-port 22. In alternative embodiments, the distance between side-port 22 and electrode 36 is about 0.5 to 2 times the outer diameter of the needle tip; the length of side-port 22 depends on the inner diameter of the needle and the outer diameter of the an intended guide-wire, and ranges from about 0.1 to 0.2 inches, or about 2.54 to 5.08 mm (about the equivalent of 3 to 6 times the outer diameter of a 0.032 inch (about 0.81 mm) guidewire); the distance between electrode distal tip 37 and side-port 22 ranges from about 0.050 to 0.125 inches (about 1.27 to 3.18 mm); and the electrode 36 has a size of about 22 to 17 Gauge (about 0.028 inches (about 0.71 mm) to about 0.058 inches (about 1.47 mm)). The electrode is large enough to provide bumper support against heart tissue.

FIG. 1D also illustrates insulation portion 32a, which covers a proximal part of side-port 22 to define an aperture 38 having a length of about 0.039 inches (about 0.99 mm). Aperture 38 is smaller than side-port 22 (uncovered). If contrast fluid is delivered through needle 20 under a constant lumen fluid pressure, the contrast will expel in a narrower stream and closer to the distal tip through an aperture 38 than through a relatively longer side-port 22.

Insulation portion 32a also reduces the amount of abrasive friction between guidewire 50 and proximal edge 30 of the side-port. First, while guidewire 50 can still rub against proximal edge 30 as it travels through the side-port, insulation portion 32a reduces the frictional forces between the guidewire and proximal edge 30. Second, when guidewire 50 travels through the side-port, it glides over insulation portion 32a, which is comprised of a polymer that is softer and less abrasive than the metal of the proximal edge 30. Insulation portion 32a further functions to direct an advancing guidewire forward, as to be further explained below.

In addition, insulation portion 32a reduces electrical leakage through side-port 22. In typical embodiments of needle 20 the tubular metal shaft tube is not insulated, which allows some electricity to leak out of the metal immediately adjacent to the side-port (i.e. metal forming the edge of the side-port), and some electricity to leak through fluid within the lumen and out of side-port 22. Insulation portion 32a covers some of the metal immediately adjacent the side-port to reduce electrical leakage therefrom. Insulation portion 32a also reduces the amount of fluid inside the lumen that is exposed to the environment outside the needle, thereby reducing electrical leakage through the fluid. Some alternative embodiments of needle 20 include insulation on an inner surface of the metal shaft tube in the area of the side-port (i.e. adjacent to) to reduce electrical leakage. Some other alternative embodiments include insulation on an inner surface of most or substantially all the metal shaft tube to reduce electrical leakage.

Another feature of needle 20 illustrated in FIG. 1D is that insulation 32 leaves a part of needle 20 adjacent to side-port 22 exposed to define elongate member exposed portion 20a. Another way to describe elongate member exposed portion 20a is that insulation 32 is trimmed back from the distal edge of side-port 22 to reduce the profile (or surface area) of the distal face of side-port 22. A reduced profile for the distal face allows a guidewire to exit the side-port at a reduced angle, i.e., closer to needle 20. Furthermore, including elongate member exposed portion 20a may help avoid a metallic guidewire adhering to insulation immediately adjacent to the side-port if a physician inadvertently electrifies the guidewire.

Figure 2:
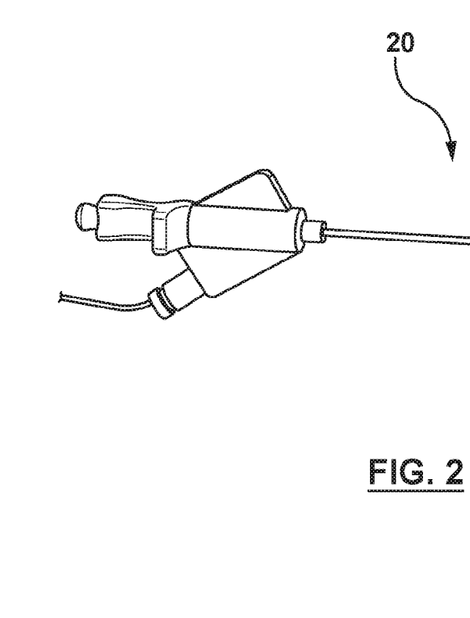
FIG. 2, including detail views 2A-2C, is an illustration of a needle having a side-port in accordance with an alternative embodiment of the invention.
Figure 2A:
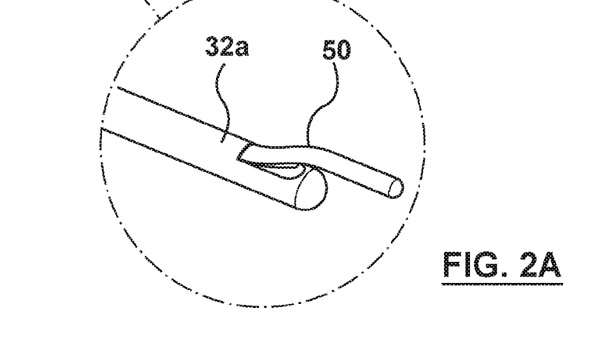
Figure 2B:
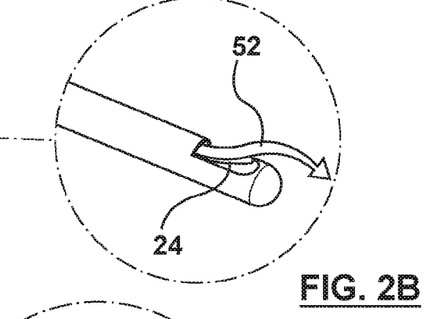
Figure 2C:
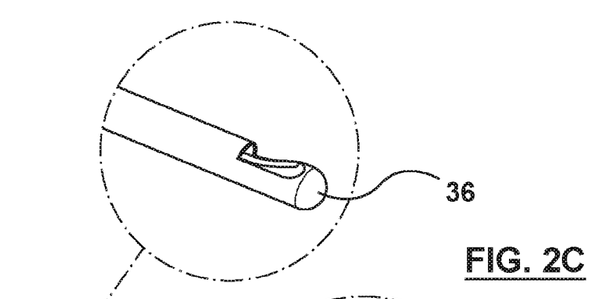
Figure 3A:
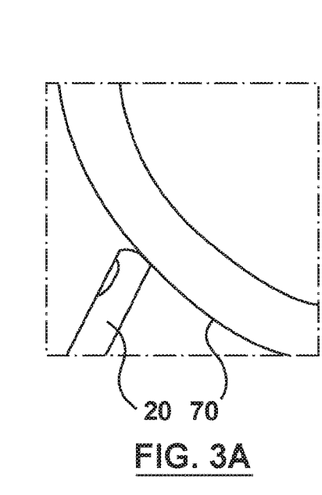
Figure 3B:
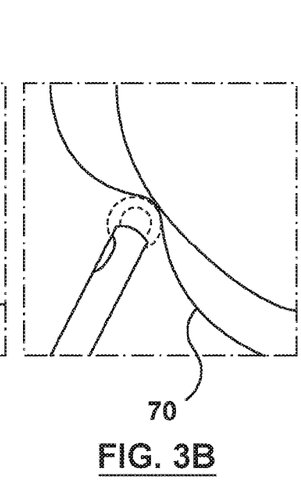
Figure 3C:
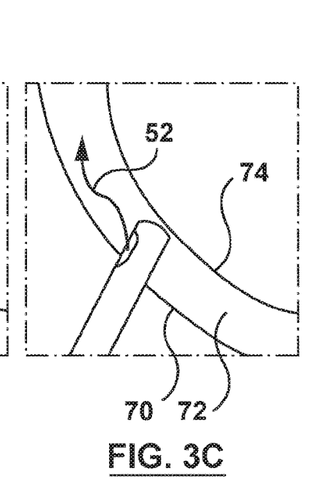
Figure 3D:
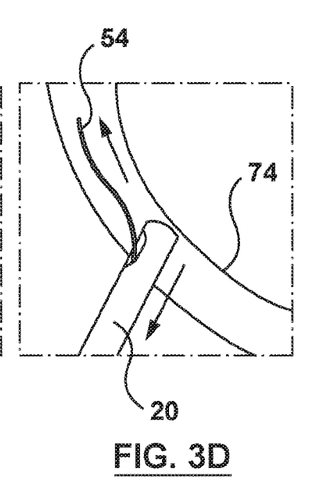
Figure 3E:
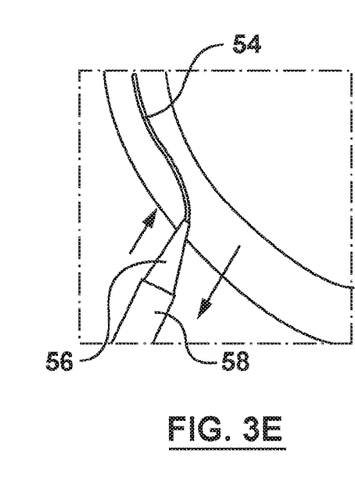
Figure 3F:
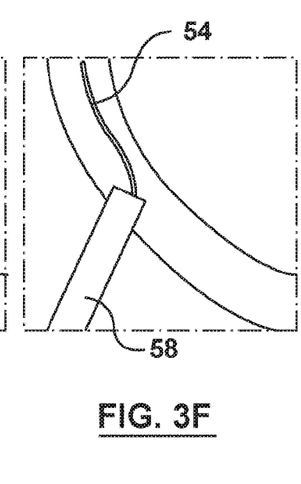
Figure 3G:
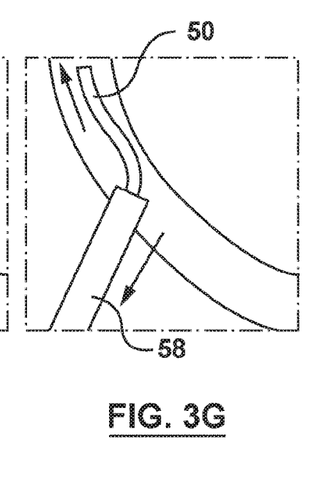
Figure 3H:
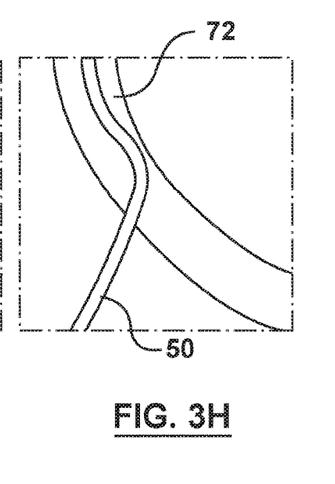
Figure 4A:
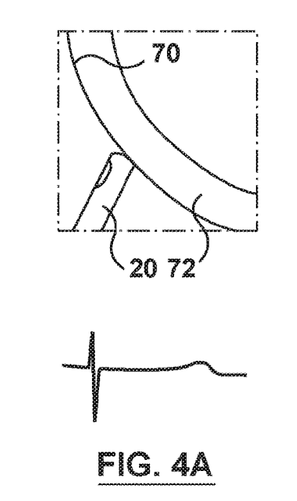
Figure 4B:
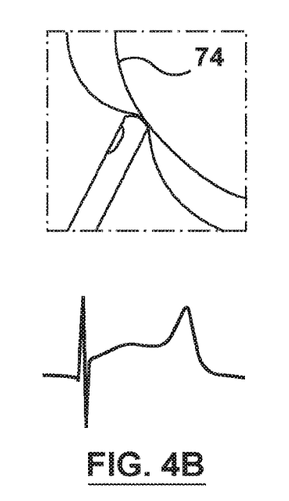
Figure 4C:
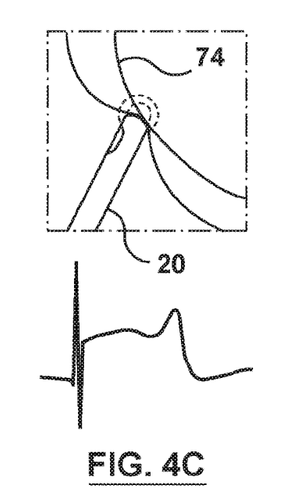
Figure 4D:
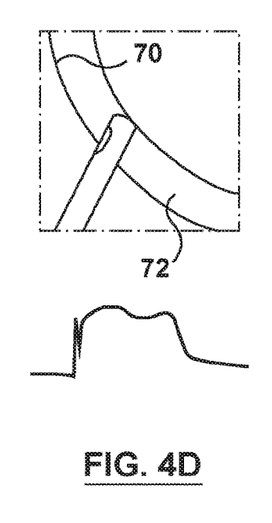
Figure 4E:
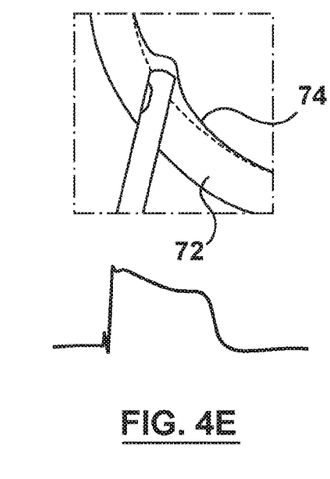
Figure 4F:
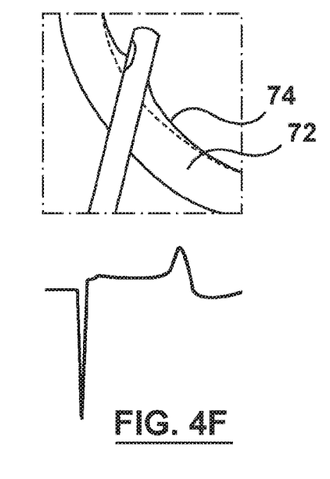

FIG. 2 illustrates an embodiment of needle 20 having a lubricious coating to enhance tactile feedback. FIGS. 2A to 2C show some of the uses of needle 20. FIG. 2A illustrates a guidewire 50 that has been advanced out of the side-port and is being advanced forwards. Guidewire 50 is guided forward by insulation portion 32a and bevel 26 of guiding surface 24. In more detail, the insulation portion 32a covers a proximal part of the side-port and a distal end of the guiding surface (or ramp) is beveled, whereby a device (e.g. a guidewire) is guided out of a side of the needle and in a forward direction when advanced out of the side-port. FIG. 2B illustrates contrast fluid injected using the side-port to create a contrast flow 52. FIG. 3 illustrates that a blunt tip comprised of electrode 36 can be used for ECG monitoring and recording. FIG. 4, consisting of FIGS. 4A-4F, illustrates some monitoring situations and the associated ECG signals. FIG. 7, consisting of FIGS. 7A-7D, shows ECG readings for different locations of the distal tip 34 of needle 20 within a pig to illustrate the advantage of ECG usage in identifying a puncture of a pericardium.

One method to fabricate a distal portion of a needle having the described geometry is to weld a metal billet, placed inside the needle lumen and flush with the needle's distal tip, to the distal end of the needle's metal shaft. The metal billet has a prefabricated guiding surface produced using milling or electrical discharge machining (EDM), and the needle shaft has a prefabricated side-port.

Another method to fabricate a distal portion of a needle is to first weld a solid metal billet flush with the distal tip of the needle's shaft, and then form the side port slot and guiding surface with an EDM electrode having a geometry corresponding to the side port and guiding surface.

FIG. 3 is an illustration showing an eight step method of using five devices, including a needle 20 disclosed herein. FIG. 3A shows a step 1 of contacting a pericardium 70 with needle 20. The heart is typically approached using a subxiphoid approach. Step 2 (FIG. 3B) includes tenting pericardium 70 with the needle and delivering energy (shown in broken line) through the blunt tip of needle 20. Step 3 (FIG. 3C) includes puncturing the pericardium 70 with the needle and injecting a contrast flow 52 into pericardial cavity 72 through a side-port of needle 20. In this example of the method, needle 20 is not touching myocardium 74, while in alternative embodiments, needle 20 touches but does not tent the myocardium 74. FIG. 3D illustrates step 4, advancing a small diameter guidewire 54 through the side-port and into the pericardial cavity 72. After the small diameter guidewire 54 is advanced, the method further includes a step 5 (FIG. 3E) of withdrawing needle 20 and advancing dilator 56 to dilate the puncture through pericardium 70. Sheath 58 may be advanced with dilator 56 or the sheath may be advanced afterwards to arrive at the illustration of FIG. 3E. Once the puncture is dilated, the method includes step 6 of advancing sheath 58 over the dilator into pericardial cavity 72 to arrive at the illustration of FIG. 3F. Step 7 includes withdrawing small diameter guidewire 54 and advancing guidewire 50 into pericardial cavity 72 (FIG. 3G). Step 8 (FIG. 3H) includes withdrawing the sheath, and leaving the guidewire 50 in pericardial cavity 72. In some embodiments guidewire 50 has a diameter of about 0.032 inches (about 0.813 mm) and small diameter guidewire 56 has a diameter of about 0.018 inches (about 0.46 mm). In some alternative embodiments, small diameter guidewire 56 has a diameter smaller than 0.018 inches (about 0.46 mm). Once guidewire 50 has been advanced into pericardial cavity 72 to provide access, other steps may include advancing a mapping catheter or some other diagnostic device, advancing an ablation catheter or some other treatment device, or placing leads or other medical devices.

FIG. 6 is an illustration showing a five step method of using two devices, needle 20 and guidewire 50. Step 1 (FIG. 6A) includes contacting a pericardium 70 using needle 20. Step 2 (FIG. 6B) includes tenting pericardium 70 with the needle and delivering energy (shown in broken line) through the blunt tip of needle 20. Step 3 (FIG. 6C) includes puncturing the pericardium 70 with the needle and injecting a contrast flow 52 into pericardial cavity 72 through a side-port of needle 20. FIG. 6D illustrates a step 4 of advancing a guidewire 50 through the needle and into pericardial cavity 72. After the guidewire 50 is advanced, the method further includes a step 5 of withdrawing needle 20 while leaving guidewire 50 in pericardial cavity 72 to arrive at the illustration of FIG. 6E. In some embodiments guidewire 50 has a diameter of about 0.032 inches (about 0.813 mm). As with the above method, once guidewire 50 has been advanced into pericardial cavity 72 to provide access, other steps may include advancing a mapping catheter or some other diagnostic device, advancing an ablation catheter or some other treatment device, or placing leads or other medical devices for example at the epicardium. Guidewire used in the two above described methods may have a straight tip or a curved tip.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A method of accessing a pericardial cavity, the method comprising the steps of: (1) contacting a pericardium with a needle, (2) tenting the pericardium with the needle and delivering energy through a blunt tip of the needle, (3) puncturing the pericardium with the needle and injecting a contrast flow into the pericardial cavity through a side-port of the needle, (4) advancing a guidewire through the needle and into the pericardial cavity, and (5) withdrawing the needle while leaving the guidewire in the pericardial cavity.

2. The method of claim 1, wherein the guidewire has a diameter of about 0.813 mm (about 0.032 inches).

3. The method of claim 1, further comprising a step after step (5) of advancing a mapping catheter.

4. The method of claim 1, further comprising a step after step (5) of advancing an ablation catheter.

5. The method of claim 1, further comprising a step after step (5) of placing leads at an epicardium.

6. The method of claim 1, wherein the guidewire has a straight tip.

7. The method of claim 1, wherein the guidewire has a curved tip.

8. A method of accessing a pericardial cavity, the method comprising the steps of: (1) contacting a pericardium with a needle, (2) tenting the pericardium with the needle and delivering energy through a blunt tip of the needle, (3) puncturing the pericardium with the needle and injecting a contrast flow into the pericardial cavity through a side-port of the needle, (4) advancing a small diameter guidewire into the pericardial cavity, (5) withdrawing the needle and advancing a dilator to dilate the puncture through the pericardium, (6) advancing a sheath over the dilator into the pericardial cavity, (7) withdrawing the small diameter guidewire and advancing a relatively larger guidewire into the pericardial cavity, and (8) withdrawing the sheath.

9. The method of claim 8, wherein a heart is approached using a subxiphoid approach.

10. The method of claim 8, wherein during step (3) the needle is not touching a myocardium.

11. The method of claim 8, wherein during step (3) the needle touches but does not tent a myocardium.

12. The method of claim 8, further comprising during step (4), advancing the small diameter guidewire through the side-port of the needle before advancing the small diameter guidewire into the pericardial cavity.

13. The method of claim 8, wherein the relatively larger guidewire has a diameter of about 0.813 mm (about 0.032 inches) and the small diameter guidewire has a diameter of about 0.46 mm (about 0.018 inches).

14. The method of claim 8, further comprising a step after step (8) of advancing a mapping catheter.

15. The method of claim 8, wherein further comprising a step after step (8) of advancing an ablation catheter.

16. The method of claim 8, further comprising a step after step (8) of placing leads at an epicardium.

* * * * *